United States Patent [19]

Frommer et al.

[11] 4,282,320

[45] Aug. 4, 1981

[54] PRODUCTION OF 1-DESOXYNOJIRIMICIN

[75] Inventors: Werner Frommer; Delf Schmidt, both of Wuppertal-1, Fed. Rep. of Germany

[73] Assignee: Bayer Aktiengesellschaft, Leverkusen, Fed. Rep. of Germany

[21] Appl. No.: 116,174

[22] Filed: Jan. 28, 1980

[30] Foreign Application Priority Data

Feb. 23, 1979 [DE] Fed. Rep. of Germany ....... 2907190

[51] Int. Cl.$^3$ .............................................. C12P 19/26
[52] U.S. Cl. ...................................... 435/84; 435/839; 435/838; 435/832
[58] Field of Search .......................................... 435/84

[56] References Cited

U.S. PATENT DOCUMENTS

| | | | |
|---|---|---|---|
| 3,634,197 | 1/1972 | Umezawa | 435/84 |
| 3,998,698 | 12/1976 | Argoudeli et al. | 435/84 |

*Primary Examiner*—Alvin E. Tanenholtz
*Attorney, Agent, or Firm*—Sprung, Felfe, Horn, Lynch & Kramer

[57] ABSTRACT

The invention relates to a novel process for the production of 1-desoxynojirimycin which involves culturing an organism of the Bacillaceae family in a nutrient solution at a temperature of about 15° to 80° C. in a fermentation vessel, whilst aerating and then isolating the 1-desoxynojirimycin, said nutrient solution containing sorbitol as the source of carbon.

7 Claims, No Drawings

PRODUCTION OF 1-DESOXYNOJIRIMICIN

The present invention relates to a new improved process for the production of 1-desoxynojirimicin.

It is known that a number of actinomycetes, above all Actinoplanaceae, form inhibitors for glycoside hydrolases, preferably carbohydrate-splitting enzymes of the gastrointestinal tract (DE-OS (German Published Specification) 2,064,092).

It is also known that nojirimicin, an antibiotic with a bacteriostatic action from strains of the genus Streptomyces, inhibits certain microbial α-glycosidases (T. NIWA et al. Agr. Biol. Chem. 34 966 (1970)).

It is furthermore known that inhibitors for glycoside hydrolases, in particular 1-desoxynojirimicin, are formed by organisms of the Bacillaceae family, especially by strains of the genus Bacillus, in customary nutrient solutions at temperatures of about 15 to about 80° C. in customary fermentation vessels, whilst aerating, culturing always taking place at a constant temperature within the temperature range indicated (DE-OS (German Published Specification) 2,726,899).

The transfer of this process, which is very good on a laboratory scale, to a larger fermenter has hitherto been accompanied by losses in yield. Surprisingly, this disadvantage could now be eliminated, and at the same time a several-fold increase in yield, compared with the laboratory process used hitherto, was achieved by changing some process parameters.

According to the present invention there is provided a process for the production of 1-desoxynojirimicin by culturing an organism of the Bacillaceae family in a nutrient solution at temperatures of about 15° to 80° C. in a fermentation vessel, whilst aerating, and then isolating the 1-desoxynojirimicin, in which sorbitol is employed as the source of carbon in the nutrient solution.

Preferably, the culturing is started at a temperature between 15° and 30° C. and the temperature is increased to 30° to 50° C. over a period covering the second half of the logarithmic growth phase and the first half of the stationary phase. Very particularly preferably, the process is furthermore carried out by a procedure in which, during multiplication of the inoculum, which is optionally stepwise multiplication, the inoculum is heated to a temperature of 80° to 100° C. and cooled again to the fermentation temperature at least once.

Particularly pure 1-desoxynojirimicin is obtained in very good yield by carrying out the isolation in the following manner. After separating off the cells, the culture solution is first adsorbed onto strongly acid ion exchangers (H+ form) and desorbed with 0.5 to 2 N ammonia solution, the active fractions are adsorbed on a weakly acid ion exchanger (H+ form) and desorbed with 0.02 to 0.1 N mineral acids, for example hydrochloric acid, the active fractions are chromatographed over a strongly basic ion exchanger (OH− form), the basic active eluate is evaporated to dryness, the residue is taken up in a polar solvent, preferably 60 to 100% strength aqueous, methanol, at elevated temperature and the product is crystallised by cooling.

Organisms of the genus Bacillus are preferably used, and the species *B. subtillis, B, subtillis* var. *niger, B, amyloliquefaciens, B, coagulas, B. longisporus* and *B. polymyxa* are particularly preferred. Of these species, the strains DSM 292, DSM 356, DSM 36, DSM 740, DSM 741, DSM 1, DMS 479, DSM 365, DSM 742, DSM 7, DSM 372, DSM 675, DSM 704, DSM 1060, DSM 1061, DSM 1062, DSM 1063, DSM 1064, DSM 1065, DSM 1066 and 1067 are preferred.

The best results are achieved with strains DSM 7 and DSM 704.

The strains are stored in the Deutsche Sammlung für Mikroorganismen (German Collection of Micro-organisms), Göttingen, and are to be obtained from this collection. Detailed descriptions of the strains, if they are stored in the DSM as patent strains, can be found in DE-OS (German Published Specification) 2,726,899. This literature source also describes, in detail, methods for discovering suitable strains, the technical use of 1-desoxymojirimicin as an inhibitor for glycoside hydrolases, test methods for establishing the inhibitory effect of 1-desoxymojirimicin as an amylase inhibitor, saccharase inhibitor and maltase inhibitor, and pharmaceutical formulations of 1-desoxymojirimicin and their preparation.

Possible sources of nitrogen for the nutrient solutions are the usual and most diverse organic substances, for example yeast extract, soya bean flour, peptones and meat extract.

The concentration of the sorbitol and of the nitrogen sources, as well as of the nutrient salts, of which $FeSO_4$, $CaCO_3$ and $MgSO_4$ may be mentioned as examples, can vary within wide limits. In some cases, separate addition of nutrient salts can be dispensed with entirely, since the complex nitrogen sources frequently contain them as concomitant materials.

Since the formation of 1-desoxymojirimicin frequently depends greatly on the composition of the nutrient media, it is advisable to culture the strains in various nutrient solutions to optimise the productive capacity. Appropriate proposals can be found in the Examples.

1-Desoxymojirimicin is a crystalline product with 540,000 SIU/g (SIU=Saccharase Inhibitor Unit; with regard to the definition, DE-OS (German Published Specification) 2,726,899, page 4, is referred to).

The compound has the structural formula

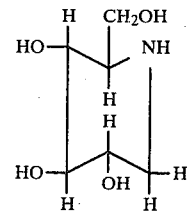

The compound was first described by S. Inoye et al. (Tetrahedron 23 2125 (1968)). The authors prepared 1-desoxynojirimicin by a chemical route by hydrogenating the antibiotic nojirimicin. The starting material nojirimicin is obtained by fermentation of organisms of the genus Streptomyces in accordance with the method of T. Niida et al. (J. Antibiotics, Ser. A. 20, 62 (1968)).

1-Desoxynojirimicin is furthermore used as a starting material for the preparation of N-substituted 1-desoxymojirimicins, which likewise have an inhibitory action on glycoside hydrolases (DE-OS(German Published Specification)2,738,717).

The following Examples illustrate the process of the present invention.

EXAMPLE 1

If a 1 liter conical flask which contains 120 ml of a nutrient solution having the composition: 6.5% by weight of glycerol, 3.0% by weight of soya bean flour, 0.2% by weight of $CaCO_3$ and tap water to make up to 100% by weight, and has been sterilised by heating to 121° C. for 30 minutes is inoculated with a spore suspension of the strain DSM 7 and the flask is incubated on a rotary shaking machine at 28° C., an activity of 630 SIU/ml is obtained after incubating for 5 days.

EXAMPLE 2

If a 1 liter conical flask which contains 120 ml of a nutrient solution having the composition: 6.5% by weight of sorbitol, 3.0% by weight of soya bean flour, 0.2% by weight of $CaCO_3$ and tap water to make up to 100% by weight, and has been sterilised by heating to 121° C. for 30 minutes is inoculated with a spore suspension of the strain DSM 7 and the flask is incubated on a rotary shaking machine at 28° C., an activity of 1320 SIU/ml is obtained after incubating for 5 days.

EXAMPLE 3

If a batch according to Example 2 is incubated at 28° C. for 45 hours and the temperature is then increased to 35° C., a culture broth with 1820 SIU/ml is obtained after a total fermentation time of 5 days.

EXAMPLE 4

If a batch according to Example 2 is incubated at 28° C. for 65 hours and the temperature is then increased to 42° C., a culture broth with 2070 SIU/ml is obtained after a total fermentation time of 5 days.

EXAMPLE 5

If a batch according to Example 2 is incubated at 28° C. for 45 hours and the temperature is then increased to 42° C., a culture broth with 2530 SIU/ml is obtained after a total fermentation time of 5 days.

EXAMPLE 6

If a 1 liter conical flask which contains 120 ml of a nutrient solution having the composition: 5.0% by weight of glycerol, 0.9% by weight of casein hydrolysate, 1.0% by weight of yeast extract, 0.1% by weight of $CaCO_3$, 0.1% by weight of $K_2HPO_4$ and tap water to make up to 100% by weight, and has been sterilised by heating to 121° C. for 30 minutes is inoculated with a spore suspension of the strain DSM 704 and the flask is incubated on a rotary shaking machine at 28° C., an activity of 25 SIU/ml is obtained after incubating for 5 days.

EXAMPLE 7

If a 1 liter conical flask which contains 120 ml of a nutrient solution having the composition: 5.0% by weight of sorbitol, 0.9% by weight of casein hydrolysate, 1.0% by weight of yeast extract, 0.1% by weight of $CaCO_3$, 0.1% by weight of $K_2HPO_4$ and tap water to make up to 100% by weight, and has been sterilised by heating to 121° C. for 30 minutes is inoculated with a spore suspension of the strain DSM 704 and the flask is incubated on a rotary shaking machine at 28° C., an activity of 120 SIU/ml is obtained after incubating for 5 days.

EXAMPLE 8

If a batch according to Example 7 is incubated at 28° C. for 45 hours and the temperature is then increased to 35° C., a culture broth with 339 SIU/ml is obtained after a total incubation time of 5 days.

EXAMPLE 9

If a batch according to Example 7 is incubated at 28° C. for 45 hours and the temperature is then increased to 42° C., a culture broth with 342 SIU/ml is obtained after a total incubation time of 5 days.

EXAMPLE 10

If a 1 ml of a batch according to Example 1 is used to inoculate again a shaking flask with the same nutrient solution and this procedure is repeated several times, as is necessary if relatively large fermenters are used the yield of SIU/ml decreases from pass to pass.

This decrease in the activity can be reduced if the culture is boiled for a short time at the end of a pass.

| Number of passes | Brief heating at the end of the Xth. pass | Final titer of the 4th pass SIU/ml |
|---|---|---|
| 4 | — | 293 |
| 4 | 3rd | 413 |
| 4 | 1st, 2nd and 3rd | 662 |

EXAMPLE 11

If a nutrient solution which has the composition: 7.5% by weight of malt extract, 0.3% by weight of casein hydrolysate, 0.7% by weight of yeast extract, 0.3% by weight of $CaCO_3$, 0.3% by weight of $K_2HPO_4$ and tap water to make up to 100% by weight, and has been sterilised by heating to 121° C. for 30 minutes and then adjusted to pH 6.6 to 6.8 with $K_2CO_3$ is treated with the strain DSM 704 in serveral passes, as in Example 6. The yield decreases from pass to pass. This decrease can be reduced if the culture is boiled for a short time at the end of each pass.

| Number of passes | Yield in SIU/ml after a Fermentation time of 6 days | |
|---|---|---|
| | without boiling | with boiling |
| 1st | 160 | 150 |
| 3rd | 145 | 138 |
| 5th | <58 | 116 |
| 6th | <41 | 135 |

EXAMPLE 12

3.6 liters of 2 M oxalic acid were added to 360 liters of the culture broth according to Example 2 and the mixture was adjusted to pH 3.2 with half-concentrated $HNO_3$. The mixture was stirred for 30 minutes and the centrifuged in an overflow centrifuge at 2,500 revolutions per minute. The 300 liters of slightly turbid supernatant liquor were passed, at a flow rate of 200 l/hour, over a 30×50 cm column packed with the strongly acid exchanger 37 Lewatit" (Trade Mark) SC 104 H + (Bayer AG).

The column was then washed with 400 liters of deionised water. The runnings and wash water were inactive and were discarded. The column was then desorbed with 130 lites of 1 N ammonia and the eluate was collected in 10 liter fractions. The active fractions 4 to 9 were combined and passed over a 15×80 cm column packed with the weakly acid exchanger "Lewatit" CNP H+ (Bayer AG). The column was washed with 150 l of deionised water and the inactive fractions comprising the runnings and wash water were discarded. The column was then eluated with 0.05 N HCl at a flow rate if 20 l/hour. The eluate was collected in 10 liter fractions, and the active fractions 3 to 10 were combined and passed over a 15 × 40 cm column packed with the strongly basic resin "Lewatit" M 500 OH− (Bayer AG). The column was subsequently eluted with distilled water. The runnings and wash water from the M 500 column were fractioned into 10 liter portions and the active fractions 1 to 12 were combined and concentrated to about 400 ml in vacuo. 1,600 ml of methanol was added to the resulting syrupy concentrate under the influence of heat (50° to 60° C.), the insoluble constituents were filtered off hot and clear filtrate was allowed to cool. After adding seed crystals, crystallisation started overnight. After 2 days at 4° C., the crystals were filtered off, washed twice with methanol, once with acetone and once with ether and dried in vacuo. Yield: 360 g of pure desoxynojirimicin base. Further crude substance can be obtained from the mother liquors of the crystallisation by further concentration.

EXAMPLE 13

The bonding of desoxynojirimicin to a strongly acid exchanger in the H+ form can also be carried out batchwise, but in this case a strongly or weakly basic ion exchanger must be added to bond the H+ ions liberated during adsorption of the substance, since desorption of the desoxynojirimicin starts at pH value 3.

7.2 kg of "Lewatit" SC 104 H+ and 2.4 kg of "Lewatit" MP 62 OH− were added to 60 liters of the fermentation batch (pH 8.0) according to Example 1 without first separating off the cells. The mixture was stirred for 30 minutes and then separated in a sieve screw centrifuge. The filtrate containing cells (pH 3.2) was inactive and was discarded. The resin was washed with distilled water and then subjected to flotation several times. The lighter "Lewatit" MP 62 resin was skimmed off and the "Lewatit" SC 104 resin which remained at the bottom and was charged with desoxynojirimicin was transferred to a 10×100 cm column and then eluted with 1 N NH₃, as described in Example 8. Further purification over "Lewatit" CNP H+ and "Lewatit" M 500 OH− and subsequent crystallisation were carried out as described in Example 12. Yield: 31 g of pure desoxynojirimicin base. If desired, separation of the mixed bed resin by flotation before the elution with ammonia can be omitted without the purity of the end product changing in any aspect.

What is claimed is:

1. A process for the production of 1-desoxynojirimicin which comprises culturing a 1-desoxynojirimicin producing strain of the Bacillaceae family in a nutrient solution containing sources of carbon and nitrogen and trace elements at temperatures of 15° to 80° C. in a fermentation vessel, whilst aerating, and then isolating the 1-desoxynojirimycin, in which sorbital is employed as the source of carbon in the nutrient solution.

2. A process according to claim 1, in which culturing is started at a temperature between 15° to 30° C. and the temperature is increased to 30° to 50° C. over a period which covers the second half of the logarithmic growth phase and the first half of the stationary phase.

3. A process according to claim 1 or 2, in which during multiplication of the inoculum, the inoculum is heated to a temperature of 80° to 100° C. and cooled again to the fermentation temperature at least once.

4. A process according to claim 3 in which the multiplication of the inoculum is stepwise multiplication.

5. A process according to claim 1 which which comprises absorbing 1-desoxynojirimicin onto a strongly acid ion exchanger (H+ form) directly from the fermentation solution or, after first separating off the cells, from the culture filtrate, and then desorbing with 0.5 to 2 N ammonia solution, adsorbing the resulting active fractions onto a weakly acid ion exchanger (H+ form) and desorbing with 0.02 to 0.1 N hydrochloric acid, chromatographing the resulting active fractions over a strongly basic ion exchanger (OH− form) evaporating the active basic eluate to dryness, taking up the residue in a polar solvent at elevated temperature and allowing the product to crystallize by cooling.

6. A process according to claim 1 in which an organism of the genus Bacillus is used.

7. A process according to claim 6, in which the strain DSM 7 or DSM 704 is used.

* * * * *

UNITED STATES PATENT AND TRADEMARK OFFICE
CERTIFICATE OF CORRECTION

PATENT NO. : 4,282,320
DATED : Aug. 4, 1981
INVENTOR(S) : Werner Frommer et al

It is certified that error appears in the above-identified patent and that said Letters Patent are hereby corrected as shown below:

Column 6, line 16    Delete "sorbital" and insert --sorbitol--.

Column 6, line 30    Delete "absorbing" and insert --adsorbing--.

Signed and Sealed this

Twelfth Day of January 1982

[SEAL]

Attest:

Attesting Officer

GERALD J. MOSSINGHOFF

Commissioner of Patents and Trademarks